United States Patent [19]

Heider et al.

[11] Patent Number: 5,683,555
[45] Date of Patent: Nov. 4, 1997

[54] WORKING UP REACTION MIXTURES OBTAINED IN ADDITION REACTIONS WITH ACETYLENE OR PROPYNE

[75] Inventors: Marc Heider, Neustadt; Michael Karcher, Schwetzingen; Martin Schmidt-Radde, Beindersheim; Albrecht Dams, Wachenheim, all of Germany

[73] Assignee: BASF Aktiengesellschaft, Ludwigshafen, Germany

[21] Appl. No.: 613,625

[22] Filed: Mar. 11, 1996

[30] Foreign Application Priority Data

Mar. 15, 1995 [DE] Germany ............... 195 09 352.6

[51] Int. Cl.$^6$ ..................................... B01D 3/34
[52] U.S. Cl. ................. 203/29; 203/63; 203/64; 203/89; 159/49; 568/693
[58] Field of Search ............... 203/89, 91, 29, 203/64, 63; 159/49; 568/673, 687–690, 693; 560/242

[56] References Cited

U.S. PATENT DOCUMENTS

| | | | |
|---|---|---|---|
| 2,806,847 | 9/1957 | Nedwick | 540/533 |
| 3,549,710 | 12/1970 | Turner et al. | 568/657 |
| 4,143,072 | 3/1979 | Hetzel et al. | 203/92 |
| 4,410,726 | 10/1983 | Parthasarathy et al. | 548/543 |
| 4,751,273 | 6/1988 | Lapin et al. | 525/455 |
| 4,828,873 | 5/1989 | Vara et al. | 427/44 |
| 5,095,154 | 3/1992 | Liu | 568/673 |

FOREIGN PATENT DOCUMENTS

| | | |
|---|---|---|
| 1812602 | 12/1968 | Germany . |
| 32 15 093 | 4/1982 | Germany . |
| 267729 | 5/1989 | Germany . |
| 3-195738 | 3/1991 | Japan . |
| 91/05756 | 5/1991 | WIPO . |

OTHER PUBLICATIONS

*Research Disclosure*, No. 290, Jun. 1988, p. 389, "Distilling organic compounds in the presence . . . ".
Liebigs Ann. Chem. 601 (1956), 81.
Ullmanns Encykopadie der . . . , 4th Ed., Verlag Chem., vol. 19, p. 31 et seq.

*Primary Examiner*—Virginia Manoharan
*Attorney, Agent, or Firm*—Keil & Weinkauf

[57] ABSTRACT

Reaction mixtures obtained in addition reactions of OH— or NH— carrying compounds with acetylene or propyne in the presence of alkali metal alcoholates or alkali metal amides are worked up by distilling off the vaporizable components from the reaction mixture in a thin-film evaporator. Before removal of the vaporizable components from the reaction mixture, a particularly defined polyether is added thereto.

6 Claims, No Drawings

WORKING UP REACTION MIXTURES OBTAINED IN ADDITION REACTIONS WITH ACETYLENE OR PROPYNE

The present invention relates to a novel process for working up reaction mixtures obtained in addition reactions of OH— or NH— carrying compounds with acetylene or propyne in the presence of alkali metal alcoholates or alkali metal amides.

The addition of OH— or NH-carrying compounds with acetylene or propyne to form vinyl ethers and N-vinyl compounds is known per se (eg. Liebigs Ann. Chem. 601 (1956), 81). The catalysts used are alkali metal alcoholates and alkali metal amides. The reaction mixtures obtained in these reactions contain distillable compounds, such as the desired adducts, and may also contain any starting compounds still present, as well as undistillable compounds, including the catalysts and polymeric byproducts of the reaction.

Simple isolation, in particular continuous isolation of the product in a manner desirable for industrial processes, is possible when the product is present in gaseous form under the reaction conditions. Owing to this limiting condition, such isolation is, however, restricted to a few products (Ullmanns Encyklopädie der technischen Chemie, 4th Edition, Verlag Chemie 1983, Vol. 23, page 608 et seq.).

In the batchwise distillation of the reaction mixtures, the undistillable components remain in the bottom of the still and must be diluted with suitable solvents and disposed of after distillation is complete (loc. cit.).

It is an object of the present invention to provide a process which can be applied to a large number of different reaction mixtures obtained in addition reactions with acetylene and propyne. In particular, it was intended to find a process which permits continuous working up of such reaction mixtures.

We have found that this object is achieved by the process defined above, which comprises distilling off the volatile components from the reaction mixture in a thin-film evaporator.

The novel process can be applied to a large number of reaction mixtures. These reaction mixtures are obtained in addition reactions of OH— or NH-carrying compounds with acetylene or propyne. Specifically alcohols, such as alkanols, preferably $C_1$–$C_{20}$-alkanols, eg. methanol, ethanol, n-propanol, isopropanol, n-butanol, isobutanol, sec-butanol, 2-ethylhexanol, dodecanol and octadecanol, nonaromatic diols, preferably $C_2$–$C_{20}$-diols, such as ethylene glycol, propylene glycol, 1,4-butanediol, 1,6-hexanediol and 1,4-cyclohexanedimethanol, and triols, such as trimethylolpropane, can be subjected to the addition reaction. Suitable NH-carrying compounds are $C_4$–$C_{10}$-lactams, such as pyrrolidone, piperidone and caprolactam, $C_2$–$C_{20}$-amides, such as N-methylacetamide, hetaryl compounds, such as pyrrole, imidazole, 2-methyl-imidazole, indole and carbazole, and ethyleneurea and secondary aliphatic amines.

Among these, octadecanol, butanediol, caprolactam, carbazole, pyrrolidone, imidazole, 2-methylimidazole and ethyleneurea are preferred.

Acetylene is the preferred alkyne.

The addition reaction of the stated OH— or NH-carrying compounds is carried out in the presence of catalysts. The alkali metal salts of the OH— or NH-carrying compounds to be subjected to the addition reaction are preferably used here. These catalysts can advantageously be prepared in situ by adding an alkali metal hydroxide to the mixture of the starting compounds.

The addition reaction is carried out in general at from 50 to 250° C. under from 1 to 25 bar in the course of from 1 to 10 hours. If necessary, an inert solvent, for example a polar aprotic solvent, such as N-methylpyrrolidone, is employed; however, a reaction in the absence of a solvent is preferred. At the end of the reaction, the reaction mixture thus obtained is preferably degassed.

The reaction mixtures contain in general from 20 to 95, preferably from 85 to 95, % by weight of product, possibly starting compounds and possibly solvents, and in general from 5 to 80, preferably from 5 to 15, % by weight of catalyst, decomposition products of the catalyst and polymeric byproducts.

According to the invention, all volatile components are distilled off from the reaction mixture in a thin-film evaporator. For this purpose, a thin film of the reaction mixture is applied to a heated surface. Such thin-film evaporators are known per se and are commercially available. Evaporators which have proven advantageous are those in which a stirrer having large paddles applies the reaction mixture continuously to the heated outer surface as a thin film. The temperature of the evaporator depends on the boiling point of the highest-boiling component in the reaction mixture. The pressure during the distillation may be from 1 mbar to 2 bar, depending on the product. As a rule, the volatile components form the distillate. They can be further purified if required, for example by distillation. The undistillable components can be removed as a viscous mass from the bottom of the evaporator.

The process described permits the continuous working up of reaction mixtures obtained in the addition reaction of OH— or NH-carrying compounds with acetylene or propyne using alkali metal alcoholates or alkali metal amides as catalysts.

In a preferred embodiment of the novel process, from 0.1 to 20, preferably from 1 to 10, % by weight of a polyether of the formula I having a molecular weight of from 200 to 10,000, preferably from 400 to 2,000, g/mol are added to the reaction mixtures before the distillation.

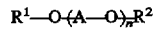

$$R^1—O—(A—O)_n—R^2 \qquad I$$

$R^1$ and $R^2$, independently of one another, are each preferably hydrogen, but alkyl, preferably $C_1$–$C_6$-alkyl, cycloalkyl, preferably $C_4$–$C_7$-cycloalkyl, and aryl, preferably phenyl, are also suitable. A is straight-chain or branched alkylene. n is an integer which may be chosen according to the radicals A so that the compound of the formula I has the abovementioned molecular weight.

The polyethers of the formula I are polymeric compounds which are derived from cyclic ethers, such as ethylene oxide, 1,2-propylene oxide, 1,3-propylene oxide or tetrahydrofuran. They are obtainable in a known manner by base-catalyzed polymerization in the presence of water or of an alcohol. The polyethers I may contain identical or different radicals A, and different radicals A may be randomly distributed or arranged in blocks (cf. Ullmanns Encyklopedie der Technischen Chemie, 4th Edition, Verlag Chemie, Vol. 19, page 31 et seq.). The molecular weight distribution of the polyethers is not critical per se, but relatively large amounts of short-chain compounds should be avoided since they may be discharged with the volatile components from the reaction mixture.

Polyethylene glycol is preferably added to the reaction mixtures.

The polyethers of the formula I are readily miscible with the reaction mixtures. They are not decomposed under the distillation conditions.

The stated polyethers result in a reduction in the viscosity of the undistillable components of the reaction mixtures. The undistillable residues thus flow more readily out of the evaporator, and blockage due to deposition of the residues in the evaporator is effectively avoided.

EXAMPLES

A constant stream of different reaction mixtures was fed continuously into a heated thin-film evaporator having stirring paddles. The distillable fraction was condensed (distillate) and the bottom product was removed from the bottom of the evaporator and collected (residue).

The distillable fraction in the residue was determined by heating the residue to above 200° C. at about 1 mbar.

A polyethylene glycol having a molecular weight of 600 g/mol was added in Novel Examples 1, 3, 5, 6, 8 and 9, a polypropylene glycol having a molecular weight of 600 g/mol was added in Example 10 and a polytetrahydrofuran having a molecular weight of 650 g/mol was added in Example 11.

The reaction mixture was prepared in each case by base-catalyzed reaction of acetylene and the corresponding OH— or NH-containing compound (for characterization, the particular product is stated).

where $R^1$ and $R^2$ are each hydrogen, alkyl, cycloalkyl or aryl, A is straight-chain or branched $C_2$–$C_6$-alkylene and n is an integer, the value of which is chosen so that the polyether has a molecular weight of from 200 to 10,000 g/mol, is added to the reaction mixture in an amount of from 0.1 to 20% by weight, based on the reaction mixture, before removing the vaporizable components from the reaction mixture, and removing residues of reduced viscosity from the bottom of the evaporator.

2. A process as claimed in claim 1, wherein the reaction mixture to be worked up is obtained by the addition reaction of a NH-carrying compound selected from the group consisting of caprolactam, carbazole, pyrrolidone, imidazole, 2-methylimidazole and ethyleneurea with acetylene.

TABLE

| Example | Reaction mixture | Amount added [% by wt., based on reaction mixture] | Pressure [mbar] | Evaporator temperature [°C.] | Distillate [g/h] | Residue [g/h] | Distillable fraction in the residue [% by wt.] | Viscosity [mPa · s] | Remarks |
|---|---|---|---|---|---|---|---|---|---|
| 1 | vinylcaprolactam | 5 | 5 | 150 | 472 | 94 | 11 | 4490–1500 | good discharge |
| 2 comparison | vinylcaprolactam | — | 4.5 | 140 | 483 | 84 | 20 | not measurable | hard residue which scarcely runs out |
| 3 | vinylimidazole | 5 | 4 | 200 | 516 | 88 | 20 | 244 | good discharge |
| 4 comparison | vinylimidazole | — | 10 | 160 | 508 | 64 | 37 | 1088 | heavy deposit in evaporator |
| 5 | cyclohexanedimethanol monovinyl ether | 5 | 10 | 200 | 526 | 42.8 | <10 | 23 | good discharge |
| 6 | octadecyl vinyl ether | 6.6 | 5 | 210 | 902 | 80 | <10 | 4.5 | good discharge |
| 7 comparison | octadecyl vinyl ether | — | 5 | 210 | 755 | 71 | <10 | not measurable | poor discharge |
| 8 | n-propyl vinyl ether | 5 | 1013 | 100 | 992 | 125 | <10 | 319–198 | good discharge |
| 9 | 1,4-butanediol monovinyl ether | 5 | 10 | 180 | 624 | 71 | <10 | not determined | good discharge |
| 10 | octadecyl vinyl ether | 5 | 7 | 220 | 652 | 68 | <10 | 15 | good discharge |
| 11 | vinylcaprolactam | 5 | 5 | 140 | 470 | 109 | 13 | 260–200 | good discharge |

We claim:

1. A process for working up a reaction mixture obtained in an addition reaction of an OH— or NH-carrying compound with acetylene or propyne in the presence of an alkali metal alcoholate or an alkali metal amide, which comprises removing vaporizable components from the reaction mixture in a thin-film evaporator, wherein a polyether of the formula I

3. A process as claimed in claim 2, wherein a polyethylene glycol of the formula I having a molecular weight of from 400 to 2,000 g/mol is used.

4. A process as claimed in claim 1, wherein the reaction mixture to be worked up is obtained by the addition reaction of an OH-carrying compound selected from the group consisting of octadecanol and butanediol with acetylene.

5. A process as claimed in claim 1, wherein a polyethylene glycol of the formula I having a molecular weight of from 400 to 2,000 g/mol is used.

6. A process as claimed in claim 1, wherein the process is carried out continuously.

UNITED STATES PATENT AND TRADEMARK OFFICE
CERTIFICATE OF CORRECTION

PATENT NO. : 5,683,555

DATED : November 4, 1997

INVENTOR(S) : HEIDER et al.

It is certified that error appears in the above-identified patent and that said Letters Patent is hereby corrected as shown below:

Column 3, claim 1, line 62, delete the formula shown as formula I and replace with:

-- $R^1-O(A-O)_nR^2$ --.

Signed and Sealed this

Twenty-seventh Day of January, 1998

Attest:

BRUCE LEHMAN

*Attesting Officer*  *Commissioner of Patents and Trademarks*